(12) United States Patent
Räsänen et al.

(10) Patent No.: US 11,525,094 B2
(45) Date of Patent: Dec. 13, 2022

(54) METHODS OF DEOXYGENATING BIO-BASED MATERIAL AND PRODUCTION OF BIO-BASED TEREPHTALIC ACID AND OLEFINIC MONOMERS

(71) Applicant: Stora Enso OYJ, Helsinki (FI)

(72) Inventors: Jari Räsänen, Imatra (FI); Ali Harlin, Vtt (FI); Olli Aaltonen, Vtt (FI); Juha Linnekoski, Vtt (FI); Jinto Anthonykutty, Vtt (FI)

(73) Assignee: Stora Enso OYJ, Helsinki (FI)

( * ) Notice: Subject to any disclaimer, the term of this patent is extended or adjusted under 35 U.S.C. 154(b) by 284 days.

(21) Appl. No.: 14/782,879

(22) PCT Filed: Apr. 8, 2014

(86) PCT No.: PCT/FI2014/050251
§ 371 (c)(1),
(2) Date: Oct. 7, 2015

(87) PCT Pub. No.: WO2014/167181
PCT Pub. Date: Oct. 16, 2014

(65) Prior Publication Data
US 2016/0046873 A1 Feb. 18, 2016

(30) Foreign Application Priority Data

Apr. 8, 2013 (FI) .................................... 20135342

(51) Int. Cl.
*C07C 4/06* (2006.01)
*C10G 3/00* (2006.01)
*C07C 51/265* (2006.01)
*C10G 9/36* (2006.01)
*C07C 51/16* (2006.01)

(52) U.S. Cl.
CPC .................. *C10G 3/50* (2013.01); *C07C 4/06* (2013.01); *C07C 51/16* (2013.01); *C07C 51/265* (2013.01); *C10G 3/46* (2013.01); *C10G 3/49* (2013.01); *C10G 9/36* (2013.01); *C10G 2300/1014* (2013.01); *Y02P 30/20* (2015.11)

(58) Field of Classification Search
CPC .............. C10G 3/50; C07C 4/06; C07C 51/16
USPC ........................................................ 562/408
See application file for complete search history.

(56) References Cited

U.S. PATENT DOCUMENTS

| 2,857,331 | A | * | 10/1958 | Hollingsworth | ....... C08G 69/34 |
|---|---|---|---|---|---|
| | | | | | 252/61 |
| 2,894,880 | A | | 7/1959 | Sisson et al. | |
| 3,649,580 | A | | 3/1972 | Herbert, Jr. et al. | |
| 4,300,009 | A | | 11/1981 | Haag et al. | |
| 4,337,193 | A | | 6/1982 | Szita | |
| 4,357,145 | A | * | 11/1982 | Dondelewski | ............ C10L 5/14 |
| | | | | | 44/568 |
| 5,023,805 | A | | 6/1991 | Aune et al. | |
| 5,457,635 | A | | 10/1995 | Scott | |
| 6,690,990 | B1 | | 2/2004 | Caron et al. | |
| 7,846,323 | B2 | | 12/2010 | Abhari et al. | |
| 7,968,757 | B2 | * | 6/2011 | Abhari | ................... C10G 45/02 |
| | | | | | 208/49 |
| 8,329,969 | B2 | * | 12/2012 | McCall | ................... C10G 3/46 |
| | | | | | 585/240 |
| 2007/0234860 | A1 | | 10/2007 | Stanish | |
| 2008/0015711 | A1 | | 1/2008 | Charland et al. | |
| 2009/0095377 | A1 | | 4/2009 | Barker | |
| 2010/0292517 | A1 | | 11/2010 | Debuisschert et al. | |

FOREIGN PATENT DOCUMENTS

| DE | 936036 | 12/1955 |
|---|---|---|
| EP | 2130812 B1 | 8/2011 |
| WO | 0167042 | 9/2001 |
| WO | 02091286 | 11/2002 |
| WO | 2005030449 | 4/2005 |
| WO | 2008039756 | 4/2008 |
| WO | 2010086507 | 8/2010 |

(Continued)

OTHER PUBLICATIONS

Pyl, Steven P., et. al. "Wood-derived olefins by steam cracking of hydrodeoxygenated tall oils," Bioresource Technology 126 (2012), 48-55.

(Continued)

*Primary Examiner* — Leigh C Maier
*Assistant Examiner* — Everett White
(74) *Attorney, Agent, or Firm* — Greer, Burns & Crain, Ltd.

(57) ABSTRACT

The present invention relates to a method of deoxygenating tall oil pitch, yielding aliphatic and aromatic hydrocarbons. The invention even comprises turning the aliphates into polymerizable olefins by steam cracking, and turning the aromates into polymerizable terephthalic acid by oxygenation and, as necessary, rearrangement. The monomers can be used for the production of polymers of partially or completely biologic origin. According to the invention, tall oil pitch is first heated to turn it into liquid, which is then fed into a catalyst bed and catalytically deoxygenated with hydrogen. The deoxygenation catalyst is preferably a Ni—Mo catalyst and, in addition, a cracking catalyst can be used, such as an acidic zeolite catalyst. The deoxygenated product stream is cooled down so as to obtain a liquid, which is distilled for separation of the aliphatic and aromatic hydrocarbons for use in the production of the respective monomers and finally polymers.

24 Claims, 1 Drawing Sheet

(56) References Cited

FOREIGN PATENT DOCUMENTS

| WO | 2011012439 A1 | 2/2011 |
|---|---|---|
| WO | 2011053166 A1 | 5/2011 |
| WO | 2011117474 | 9/2011 |
| WO | 2011151528 | 12/2011 |

OTHER PUBLICATIONS

Anthonykutty, Jinto Manjaly, et. al. "Upgrading of fatty acid containing rosin acids in to high value hydrocarbons via catalytic hydrodeoxygenation," Sep. 2011.
Repyakh, S. M., et. al. "Destructive Hydrogenation of Tall Oil Pitch," Siberian Technological Institute, 106-108.
Chiu, Ying-Chech "Tall Oil Pitch in Chemical Recovery," Society of Petroleum Engineers Journal, Dec. 1980, 439-449.
Anthonykutty, Jinto M., et. al. "Renewable feedstock for steam crackers: Catalytic upgrading of crude tall oil (CTO) into bio-naphtha," Jan. 2013.
Holmbom, B., et. al. "Composition of Tall Oil Pitch," Journal of the American Oil Chemists' Society vol. 55, Mar. 1978, 342-344.
Arizona Chemical, "Sylfat DP-8 Pitch Product Data Sheet," Jan. 2011.
Holblom et al., Journal of the American Oil Chemists' Society, Mar. 1978, vol. 55, Issue 3, pp. 342-344.
Senseman, C.E., Stubbs, J.J., "Catalytic Oxidation of p-Cymene in the Vapor Phase," Ind. Eng. Chem., 1931, 23 (10), p. 1129.
Sharma, Ramesh K., and Bakhshi, Narendra N., "Catalytic Conversion of Crude Tall Oil to Fuels and Chemicals Over HZSM-5: Effect of Co-Feeding Steam," Fuel Processing Technology, 27 (1991), 113-130.
Internal Searching Authority, International Search Report, PCT/FI2014/050281, dated Jun. 17, 2014.
Holmbolm, B., Composition of Tall Oil Pitch, Journal of the American Oil Chemists' Socieity, vol. 55, No. 3, pp. 342-344 (1978).

\* cited by examiner

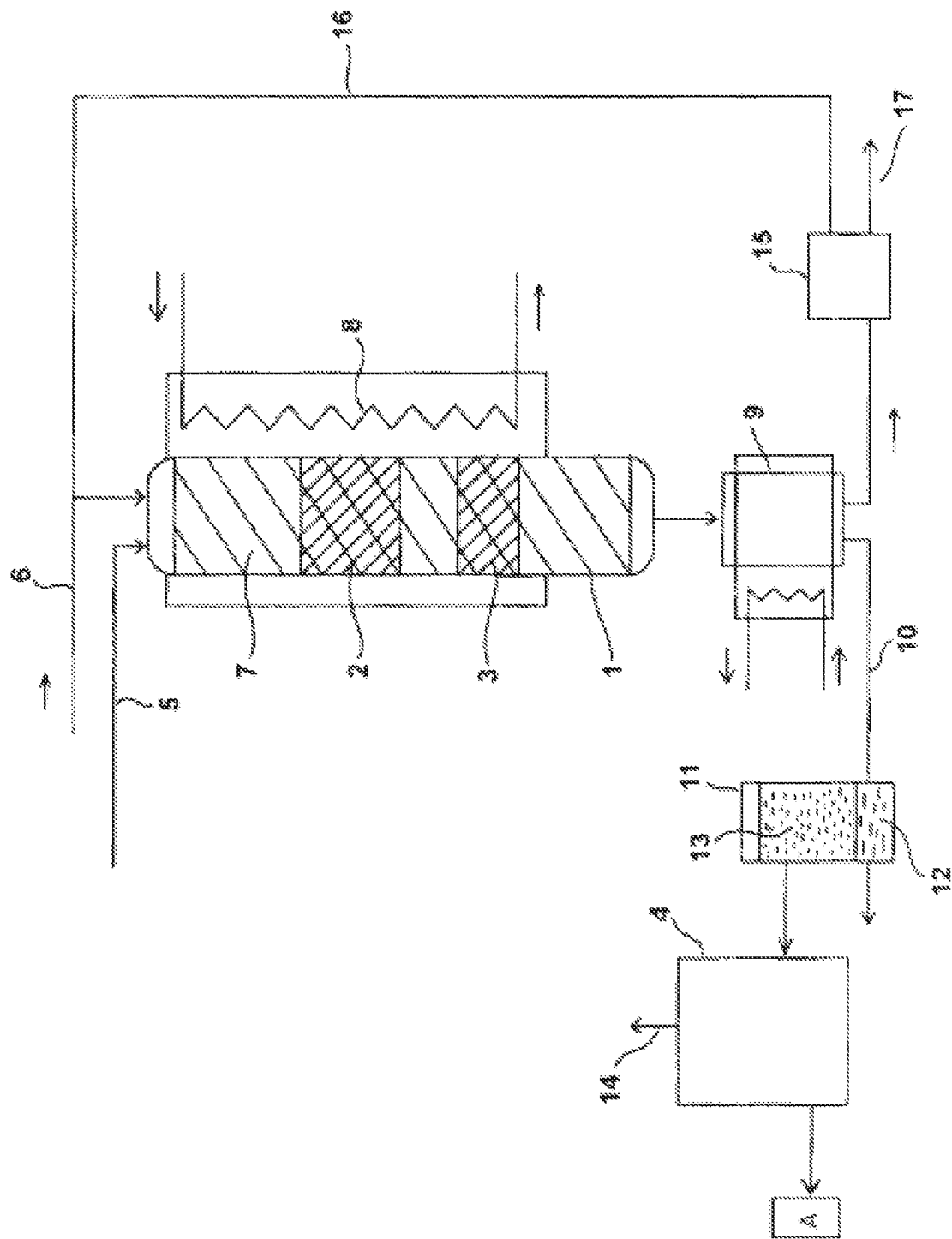

METHODS OF DEOXYGENATING BIO-BASED MATERIAL AND PRODUCTION OF BIO-BASED TEREPHTALIC ACID AND OLEFINIC MONOMERS

This application is a U.S. National Phase under 35 U.S.C. § 371 of International Application No. PCT/FI2014/050251, filed Apr. 8, 2014, which claims priority under 35 U.S.C. §§ 119 and 365 to Finnish Application No. 20135342, filed Apr. 8, 2013.

The present invention relates to a method of deoxygenating a bio-based material, which is tall oil pitch containing a considerable share of fatty and resin acids and/or their derivates, especially esters.

Further objects of the invention are methods for the preparation of terephthalic acid and the preparation of olefinic monomers, such as ethylene and propylene, from tall oil pitch, these methods comprising the above-mentioned deoxygenation as the first step. The monomeric products are useful materials for the production of biopolymers, such as polyethylene (PE), polypropylene (PP), polyethylene terephthalate (PET) and polybutylene terephthalate (PBT).

The invention even comprises use of tall oil pitch as well as use of the above-mentioned intermediate monomeric products for the production of biopolymers PE, PP, PET and PBT.

Polymers have conventionally been produced from crude oil of fossil origin. In recent times biopolymers made from renewable raw materials have increasingly been studied as an alternative. One such raw material is tall oil obtained as a by-product from cellulosic pulp cooking process.

In WO 2008/039756 A1 there is described cracking of a wood-based material into a naphtha boiling point range liquid. The starting material of the process comprises waste cellulose or lignin, which is soaked in tall oil that forms a liquid carrier. The slurry is subjected to a catalytic hydrocracking process using metal, such as Ni and Mo, combined with a zeolite or silica alumina catalyst. The product is obtained as steam, which is condensed into liquid, and any excess hydrogen can be circulated in the process. Cracking removes oxygen from the product, and molecules are cracked into smaller ones. The general aim is the production of fuels and chemical intermediate products, even if also monomers for the production of plastics are passingly mentioned.

Tall oil contains fatty acids and resin acids, which can be subjected to catalytic hydrodeoxygenation (HDO) and cracking, yielding a hydrocarbon-bearing liquid product as well as gas and water. The liquid hydrocarbons have been turned to biofuels, but there is also literature on turning them to monomeric compounds, which can serve as starting materials for the production of polymers.

WO 2010/086507 teaches a process for the production of polymerizable ethylene and propylene from a distilled mixture of at least 75% of tall oil fatty acids and no more than 25% of tall oil resin acids, which is subjected to catalytic deoxygenation with hydrogen, followed by subjecting the yield of liquid hydrocarbons to steam cracking, which yields said monomers.

WO 2011/151528 describes catalytic hydrodeoxygenation of various tall oil materials, such as crude tall oil (CDO), distilled tall oil (DTO) or tall oil fatty acids (TOFA), followed by separation of suitable aromatic hydrocarbons such as p-xylene or o-xylene from the liquid product and oxidizing them to terephthalic acid useful for the production of polyethylene terephthalate of biologic origin (bio-PET).

A feature of the process of WO 2011/151528 differing from that of WO 2010/086507 is its use of starting materials rich in resin acids, which are useless as a raw material source for the production of aliphatic hydrocarbons and hydrocracked olefins according to the latter, and even otherwise poorly tolerated therein. In order to increase the yields in general it would be desirable to broaden the choice of starting materials, to crude tall oil or even beyond, instead of acids purified by distillation.

U.S. Pat. No. 4,300,009 describes in example 18 cracking of tall oil pitch by means of hydrogen and a zeolite HZSM-5 catalyst, yielding hydrocarbons at a 40% conversion of the pitch. The result suggests that no substantial deoxygenation of the pitch was achieved. Separation of the hydrocarbon yield from the rest of the material would be difficult also.

BRIEF DESCRIPTION OF THE DRAWING

FIG. 1 is a schematic of a method of the present invention.

The problem to be solved by the invention is to achieve an improved process allowing use of a new and cheaper raw material for catalytic hydrodeoxygenation as well as subsequent process steps obtaining polymerizable compounds, without the need of distilling or otherwise purifying tall oil, without deterioration of the catalyst, and with improved yield of both aliphatic and aromatic hydrocarbons from the deoxygenating step. This would allow parallel production of polyolefins and e.g. polyethylene terephthalate from a single plentiful raw material source.

The solution provided by the invention is use of tall oil pitch as the bio-based starting material for the process. Hence, according to a first aspect of the invention, there is provided a method of deoxygenating tall oil pitch, wherein
 tall oil pitch, which contains a share of fatty and resin acids and/or their derivatives, is heated to a temperature sufficient to turn it liquid;
 said liquid is fed into a catalyst bed, to bring it into contact with hydrogen and one or more catalysts in said catalyst bed;
 the feed is catalytically deoxygenated with hydrogen; and
 a gaseous effluent from the bed is cooled down, to yield a liquid product, which comprises aliphatic and aromatic hydrocarbons and which has been substantially completely deoxygenated.

According to a second aspect of the invention there is provided a method of producing bio-based terephthalic acid, wherein
 tall oil pitch, which contains a share of fatty and resin acids and/or their derivatives, is heated to a temperature sufficient to turn it liquid;
 said liquid is fed into a catalyst bed, to bring it into contact with hydrogen and one or more catalysts in said catalyst bed;
 the feed is catalytically deoxygenated with hydrogen;
 a gaseous effluent from the bed is cooled down, to yield a liquid intermediate product, which comprises aliphatic and aromatic hydrocarbons and which has been substantially completely deoxygenated;
 an aromatic hydrocarbon that can be converted into terephthalic acid is separated from said intermediate product; and
 the separated hydrocarbon is subjected to oxygenation and a possible rearrangement reaction, so that terephthalic acid is obtained as the end product.

According to a third aspect of the invention there is provided a method of producing olefinic monomers for the production of a polymer, wherein tall oil pitch, which contains a share of fatty and resin acids and/or their derivatives, is heated to a temperature sufficient to turn it liquid;

said liquid is fed into a catalyst bed, to bring it into contact with hydrogen and one or more catalysts in said catalyst bed;

the feed is catalytically deoxygenated with hydrogen;

a gaseous effluent from the bed is cooled down, to yield a liquid intermediate product, which comprises aliphatic and aromatic hydrocarbons and which has been substantially completely deoxygenated;

a fraction rich in aliphatic hydrocarbons is separated from said intermediate product; and said fraction is subjected to steam cracking to obtain a product, which contains polymerizable olefins.

Tall oil pitch is a solid fraction, which is obtained as a non-distillable residue from vacuum or steam distillation of crude tall oil. The composition of tall oil pitch varies and cannot be defined exactly, but free fatty acids and resin acids, esterified fatty and resin acids, and unsaponifiable neutral compounds, including fatty alcohols, diterpenes and sterols are usually reported as major components, the share of fatty and resin acids and their derivatives being about 40-90 wt-% and the share of terpenes about 50 wt-% at most. For the composition reference is even made to Holblom et al *Journal of the American Oil Chemists' Society*, March 1978, Vol 55, Issue 3, p. 342-344. Tall oil pitch may form up to 40 wt-% of crude tall oil, and has been regarded as a waste of limited value. Up to now it has found use as rubber component, asphalt component, surfactant, drilling mud component and asphalt binder for instance. However, most tall oil pitch has been burnt as a source of energy.

However, the major components of tall oil pitch are free acids quite similar to those in distilled tall oil, or closely related derivatives thereof. Tall oil pitch is rich particularly in abietic, pimaric, oil and linoleic acids and their derivates. Secondly, tall oil pitch is easily softened and turned into liquid by mild heating, to about 55° C., and may then be supplied as a feed to a hydrodeoxygenating reactor just as tall oil may at room temperature. As the temperature in the reactor is high anyway, in the range of 300-450° C., nothing but slight heating is needed to manage feeding it to the process. Catalysts known to deoxygenate and crack fatty as well as resin acids, i.e. effective for crude tall oil, may be used to treat those components in tall oil pitch also.

The resin acids and their esters present in tall oil pitch may thus be deoxygenated catalytically into monoaromates, such as benzene, toluene, and xylene in connection with the hydrogen treatment. The monoaromates, such as p-xylene, m-xylene, o-xylene, or p-cymene, which are suitable for the manufacture of terephthalic acid, can be separated from the liquid phase of the reaction yield of the catalyst stage by fractional distillation.

The separation and further processing of monoaromates is a technique that pertains to normal petrochemistry; therefore, it is easy to implement the process according to the invention, in practice.

According to the invention a more than 99% conversion of the oxygenous components of tall oil pitch to hydrocarbons may be achieved. The hydrocarbon yield would have an oxygen content of 0.1% or less, down from about 8.5-10% in the pitch. Such a high deoxygenation is essential for successful turning of the yield to olefin or aromatic monomers.

In the invention a deoxygenating metal catalyst such as NiMo can be used or, optionally, a combination of deoxygenation and cracking catalysts comprising metal and zeolite catalysts, e.g. a combination of NiMo and ZSM-5. The requirement is that no polycycles or deposits are created in the catalyst, as opposed to acidic montmorolite, which has been used as a catalyst for tall oil deoxygenation and which disturbs the process.

The metal catalyst may be presulfided, e.g. in the form of NiMoS, so as to be effective in removal of sulphur present in tall oil pitch. Thus a 90% removal of sulphur may be achieved in the process.

The catalytic hydrodeoxygenation works by releasing oxygen from fatty acids and forming water, carbon monoxide and/or carbon dioxide. No significant breaking of carbon chains into smaller molecules happens yet, which is advantageous for the recovery of aromates. In the invention, the exploitation of the catalytic fixed bed can be limited to the deoxygenation stage.

The fatty acids and their esters present in tall oil pitch may be deoxygenated catalytically into aliphatics, which can be separated from the liquefied product by distillation and turned into olefinic monomers by conventional steam cracking.

An alternative application of the invention is that the deoxygenation is followed by catalytic cracking in the fixed bed to reduce molar mass, whereby the catalysts of the deoxygenation and cracking stages are different from each other and located apart from each other in the bed. Cracking creates unsaturated hydrocarbons and releases hydrogen, so that the hydrogen-bearing gas exiting them is preferably circulated back to the deoxygenation stage. In that case, it is even possible that the process requires an external source of hydrogen at the initiation stage only, and simply works thereafter by the circulated hydrogen.

As the catalyst of the cracking in the fixed bed, acidic catalysts can be used, such as an acidic zeolite catalyst or montmorolite catalyst. As the catalyst of the deoxygenation stage, regardless of the possible catalytic cracking, a metallic catalyst, such as NiMo or CoMo, can be used. The latter are reduced with hydrogen and treated with hydrogen sulfide in a well-known manner. In the method according to the invention, the NiMo catalyst is preferable, because it produces aromates from the CTO feed with a high yield, but is not sensitive to coking.

The catalyst of the cracking stage is preferably acidic, such as the acidic zeolite catalyst, preferably the ZSM-5 catalyst.

By the means of suitable catalysts, hydrodeoxygenation and considerable catalytic cracking can take place in the bed simultaneously. Such catalysts include nickel-bearing Y zeolite (NiY zeolite) or nickel-bearing montmorolite (NiSMM), which require a high hydrogen pressure in the reactor. NiSMM also cracks resin acids and is, thus, particularly advantageous for the effective exploitation of the tall oil components.

A suitable reaction temperature at the hydrodeoxygenation and possible catalytic cracking stages is within 300-450° C., preferably 320-430° C. and most preferably 350-400° C. At lower temperatures there is a risk of polymerization, and at higher temperatures there is a risk of coking; already when feeding the fatty acids into the reactor. To avoid coking, a preferable temperature is within 320-400° C. With advantage the temperature may be raised so as to be within 320-370° C. at the start of the catalytic process and within 370-430° C. at the end of said process.

A suitable pressure at the hydrodeoxygenation and cracking stages is 50-100 bars. The processing is preferably continued for 30-60 minutes, more preferably 35-50 minutes.

The weight hourly space velocity (WHSV) in the catalyst bed is preferably 0.2-1.0 1/h.

As regards the production of terephthalic acid, this is conventionally obtained from p-xylene by oxidation, in particular. Other forms of xylene (meta and ortho) can be converted to be suitable, for example, by the Henkel reaction or its modification. The Henkel reaction is an industrial-scale process, wherein the alkali salts of aromatic acids are re-arranged using a thermal reaction in the presence of a metallic salt, such as cadmium salt (DE 936036).

According to a preferred embodiment, the method according to the invention is carried out by catalytically converting the raw material by separating a suitable xylene isomer from the liquid phase of the reaction yield, for example, by distillation, and by carrying out the stages subsequent to the separation, according to formula 1:

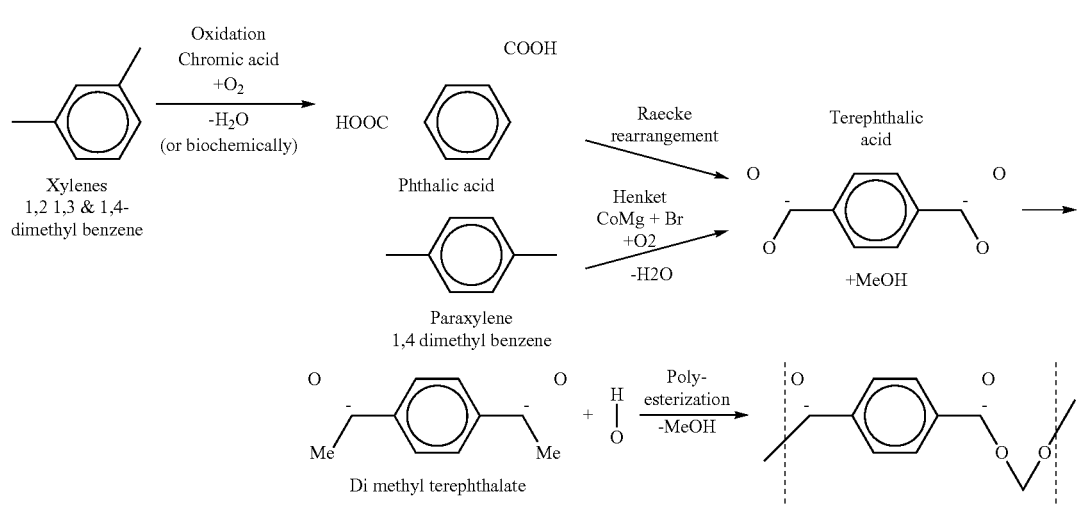

Formula 1

The oxidation can be carried out with a suitable chemical or biochemical oxidizer, preferably chromic acid. Depending on the selected xylene isomer, phthalic acid or terephthalic acid is obtained as a result of the oxidation.

The phthalic acid obtained is converted into terephthalic acid by the Raecke (Henkel) rearrangement reaction, which is preferably carried out using a salt catalyst, which in the present invention most preferably comprises cobalt magnesium salt.

According to the Henkel rearrangement reaction, a salt of the source material acid is formed from the source material acid and the salt catalyst, which thereafter is heated to a temperature of at least 300° C., preferably 330-500° C., more preferably 350-450° C., most suitably in an inert gas atmosphere. As a result, the salt of terephthalic acid is obtained.

Regarding the conversion of p-cymene into terephtalic acid, a reference is made to the publication Senseman, C. E., Stubbs, J. J., Ind. Eng. Chem., 1931, 23 (10), p. 1129.

When so desired, the obtained terephthalic acid can be esterified using any alcohol suitable for the purpose, such as methanol, and the dimethyl or corresponding terephthalate obtained as a result of the reaction of which can be polymerized into a desired polyester in a well-known manner.

Correspondingly, from the bio-based terephthalic acid produced according to the invention, bio-based polyesters, such as polyethylene terephthalate and polybutylene terephthalate, can be manufactured by polymerizing it with a bio-based diol.

Either the bio-based monomers produced according to the invention can be used to increase the bio monomer portion of a polymer still partially based on fossil raw material, or those bio-based monomers can be used exclusively for the production of a fully bio-based polymer.

In the following the invention is described in more detail with reference to the appended drawing (FIG. 1), which schematically presents an equipment that is intended for carrying out the invention.

The basic stages of the hydrodeoxygenation and cracking processes of tall oil pitch according to the drawing are the catalytic deoxygenation and cracking stages 2, 3 that take place in a vertical reactor 1, and the further processing of the liquid hydrocarbons obtained from these stages comprising distillation 4 to divide them to aliphates and aromates, which are treated in their respective ways as such known in the field of petrochemistry. Tall oil pitch, which may comprise 55-90 wt-% of free or esterified fatty acids and resin acids, together with unsaponifiable neutral compounds, is fed to an upper end of the reactor 1. In addition, hydrogen is supplied to the upper end of the reactor 1 from a line 6. The reactor 1 is filled with quartz wool that works as bed material 7, its superimposed zones 2, 3, which are apart from each other, having a metal (e.g. NiMo or NiMoS) catalyst to deoxygenate the acid components of the pitch feed and to desulfurize the feed, and zeolite or montmorillonite catalyst to crack the carbon chains. The flow direction of the liquid and gas phases in the reactor 1 is from top to bottom. To adjust the reaction temperatures, the reactor 1 is provided with an electric heater 8.

The hot reaction products that exit through the lower end of the reactor 1 are conducted to a cooler 9, and the liquefied product moves through a line 10 to a separating tank 11, which separates the aqueous phase 12 from the oil phase 13. The oil phase 13, the main components of which are saturated aliphatic hydrocarbons as well as aromatic hydrocarbons, is subjected to distillation 4, where aromates A are recovered and further processed by the processes according to prior art and where aliphates 14 are subjected to steam cracking to obtain low-molecular olefins. The olefins can be turned into biopolymers, such as polyethylene or polypropylene, by use of known techniques. Monoaromates that can be converted into terephtalic acid are separated from other aromates and processed by oxygenation and rearranging as necessary. Polyethylene terephthalate is obtained by polymerization with a diol by known methods.

The gas, which is not condensed in the cooler 9 and which contains hydrogen, oxides of carbon, possible low-molecular hydrocarbons and other impurities, moves to a purifier 15, which separates hydrogen from the other gas components. Pure hydrogen is circulated through the line 16 back to the upper end of the reactor 1 so as to constitute the deoxygenation gas, and the oxides of carbon and other impurities 17 are removed from the process.

EXAMPLE

A sample of tall oil pitch was used for the tests. An analysis of the pitch feed is included in Table 1 below. Sesquiterpene and terpene alcohols are difficult to separate from each other and are only presented as a group. An elemental analysis of the pitch feed is found in Table 2 below.

A six hour run in a reactor as shown in FIG. 1 was performed. The pitch was melted by heating and fed to the reactor for deoxygenation and cracking. Hydrogen was used as the deoxygenating gas. The deoxygenation catalyst was NiMo presulfided with $H_2S$ and $H_2$ at 320° C., to form NiMoS. The initial deoxygenation temperature in the test was about 330° C. and rose to about 400° C. towards the lower end of the reactor. The gas pressure was about 50 bar. The liquid and gas products were collected, and the liquid was analysed. The shares of the components of the pitch feed as found in the liquid yield are included in Table 1. An elemental analysis of the liquid yield is included in Table 2.

TABLE 1

|  | In feed wt-% | In the product wt-% (6 hour run) |
|---|---|---|
| Free fatty acids | 20.5 | 0.20 |
| Bound fatty acids | 10.2 | 0.02 |
| Free resin acids | 13.4 | <0.04 |
| Bound resin acids | 1.6 | <0.04 |
| Sterols | 5.7 | <0.1 |
| Monoterpenes | ~5 | <1 |
| Sesquiterpene and terpene alcohols | ~30 | ~5 |

TABLE 2

|  |  |  |  | In feed | In the product |
|---|---|---|---|---|---|
| carbon | C | % | ASTM D 5373 | 79.8 | 85.7 |
| hydrogen | H | % | ASTM D 5373 | 10.8 | 13 |
| nitrogen | N | % | ASTM D 5373 | <0.1 | <0.1 |
| Sodium | Na | mg/kg | wet combustion + ICP-OES | 810 | <5 |
| Kalium | K | mg/kg | wet combustion + ICP-OES | 82 | <5 |
| Sulphur | S | mg/kg | wet combustion + ICP-OES | 3100 | 270 |
| Phosphorus | P | mg/kg | wet combustion + ICP-OES | 56 | <5 |
| Iron | Fe | mg/kg | wet combustion + ICP-OES | 17 | <1 |
| Calcium | Ca | mg/kg | wet combustion + ICP-OES | 73 | <5 |

The bulk of the liquid yield was formed by hydrocarbons. The shares of N-alkanes, naphthenes and aromatics in the yield were 48.1 wt-%, 47.5 wt-% and 4.3 wt-%, respectively.

The yield was rich in octadecane and heptadecane in particular, their shares being 22.5 wt-% and 16.7 wt-%, respectively.

The results show that tall oil pitch can be effectively used for the production of oxygen-free liquid hydrocarbons. The process removes more than 99%, even more than 99.9%, of the oxygen contained in the pitch feed, and even removes more than 90% of the sodium content of the pitch from the liquid product. The resulting liquid hydrocarbons is separable into a major aliphatic fraction and a minor aromatic fraction by distillation, the former being convertible into olefins by hydrocracking and the latter being convertible into terephthalic acid by known means as described in the above.

The invention claimed is:

1. A method of deoxygenating tall oil pitch, wherein
   tall oil pitch obtained as a non-distillable residue from vacuum or steam distillation of crude tall oil, which contains a share of fatty and resin acids and/or their derivatives, is heated to a temperature sufficient to turn it liquid;
   said liquid is fed into a catalyst bed formed by a solid bed material, to bring it into contact with hydrogen and at least two catalysts in said catalyst bed, said catalysts including a NiMo deoxygenation catalyst and a cracking catalyst which are different from each other and located sequentially apart from each other in the catalyst bed;
   the feed is catalytically deoxygenated with hydrogen;
   the feed is cracked by means of the cracking catalyst; and
   a gaseous effluent from the bed is cooled down, to yield a liquid product, which comprises aliphatic and aromatic hydrocarbons and which has been substantially completely deoxygenated:
   wherein conversion of the oxygenous components of the feed to hydrocarbons is above 99%.

2. The method of claim 1, wherein the tall oil pitch is heated to the temperature of at least 55° C. to turn it liquid.

3. The method of claim 1 wherein the liquid yield is divided into a fraction rich in aliphatic hydrocarbons and a fraction rich in aromatic hydrocarbons.

4. The method of claim 1 wherein one of the catalysts of the deoxygenation stage is a catalyst comprising NiMoS.

5. The method of claim 1 wherein one of the catalysts of the cracking stage is acidic.

6. The method of claim 5 wherein the acidic catalyst is a ZSM-5 zeolite catalyst.

7. The method of claim 1 wherein the deoxygenation is carried out at a temperature of 300-450° C.

8. The method of claim 7 wherein the deoxygenation is carried out by raising the temperature so as to be within 320-370° C. at the start of the process and within 370-430° C. at the end of the process.

9. The method of claim 1 wherein the deoxygenation is carried out at a pressure of 50-100 bars.

10. The method of claim 1 wherein the weight hourly space velocity (WHSV) in the catalyst bed is 0.2-1.0 1/h.

11. The method of claim 1 wherein water contained in the liquid yield is separated from the produced liquid hydrocarbons.

12. The method of claim 1 wherein one or more aromatic hydrocarbons that can be converted into terephtalic acid are separated from the reaction yield by distillation.

13. The method of claim 1 wherein the aromatic hydrocarbon that is separated from the reaction yield is o-xylene, m-xylene or p-xylene, or a cymene.

14. A method of producing bio-based terephthalic acid, wherein tall oil pitch obtained as a non-distillable residue from vacuum or steam distillation of crude tall oil, which tall oil pitch contains a share of fatty and resin acids and/or their derivatives, is heated to a temperature sufficient to turn it liquid;

said liquid is fed into a catalyst bed formed by a solid bed material, to bring it into contact with hydrogen and at least two catalysts in said catalyst bed, said catalysts including a NiMo deoxygenation catalyst and a cracking catalyst which are different from each and located sequentially apart from each other in the catalyst bed;

the feed is catalytically deoxygenated with hydrogen;

the feed is cracked by means of the cracking catalyst;

a gaseous effluent from the bed is cooled down, to yield a liquid intermediate product, which comprises aliphatic and aromatic hydrocarbons and which has been substantially completely deoxygenated;

an aromatic hydrocarbon that can be converted into terephthalic acid is separated from said intermediate product; and the separated hydrocarbon is subjected to oxygenation and a possible rearrangement reaction, so that terephthalic acid is obtained as the end product;

wherein conversion of the oxygenous components of the feed to hydrocarbons is above 99%.

15. The method of claim 14 wherein oxygenation of the separated hydrocarbon is carried out with a chemical or biochemical oxidizer.

16. The method of claim 15 wherein the oxidizer is chromic acid.

17. The method of claim 14 wherein p-xylene is separated from the said intermediate product and oxidized into terephthalic acid.

18. The method of claim 14 wherein o-xylene is separated from the said intermediate product and oxidized into phthalic acid, which thereafter is converted by means of the Raecke or Henkel rearrangement reaction into terephthalic acid.

19. The method of claim 18 wherein the conversion into terephthalic acid is carried out by using a salt catalyst.

20. The method of claim 19, wherein the salt catalyst is a cobalt-magnesium salt.

21. The method of claim 14 wherein in the rearrangement, the reaction mixture is heated to a temperature of at least 300° C., in an inert gas atmosphere.

22. The method of claim 21 wherein the reaction mixture is heated to a temperature of 330-500° C.

23. A method of producing olefinic monomers for the production of a polymer, wherein tall oil pitch obtained as a non-distillable residue from vacuum or steam distillation of crude tall oil, which tall oil pitch contains a share of fatty and resin acids and/or their derivatives, is heated to a temperature sufficient to turn it liquid;

said liquid is fed into a catalyst bed formed by a solid bed material, to bring it into contact with hydrogen and at least two catalysts in said catalyst bed, said catalysts including a NiMo deoxygenation catalyst and a cracking catalyst which are different from each and located sequentially apart from each other in the catalyst bed—the feed is catalytically deoxygenated with hydrogen;

the feed is cracked by means of the cracking catalyst;

a gaseous effluent from the bed is cooled down, to yield a liquid intermediate product, which comprises aliphatic and aromatic hydrocarbons and which has been substantially completely deoxygenated;

a fraction rich in aliphatic hydrocarbons is separated from said intermediate product; and said fraction is subjected to steam cracking to obtain a product, which contains polymerizable olefins;

wherein conversion of the oxygenous components of the feed to hydrocarbons is above 99%.

24. The method of claim 23, wherein ethylene and/or propylene are produced by the steam cracking.

* * * * *